US00PP09584P

United States Patent [19]

Fuess

[11] Patent Number: Plant 9,584

[45] Date of Patent: Jun. 18, 1996

[54] CHRYSANTHEMUM NAMED 'EMPIRE CALYPSO'

[76] Inventor: Janet S. Fuess, 22 Country Club Dr., New York Mills, N.Y. 13417

[21] Appl. No.: 439,143

[22] Filed: May 11, 1995

[51] Int. Cl.[6] ..... A01H 5/00

[52] U.S. Cl. ..... Plt./76

[58] Field of Search ..... Plt./76, 81, 82

*Primary Examiner*—Howard J. Locker

*Attorney, Agent, or Firm*—Foley & Lardner

[57] ABSTRACT

A new and distinct cultivar of Chrysanthemum plant named Empire Calypso, characterized by its red-purple ray florets; fully double flowers; compact, mounded cushion habit; 4.0–4.5 cm capitulum diameter; natural season flower date of September 20; and seven week flower response in light/shade programs.

1 Drawing Sheet

The present invention comprises a new and distinct cultivar of Chrysanthemum, botanically known as *Dendranthema grandiflora*, and hereinafter referred to by the cultivar name Empire Calypso.

Empire Calypso is a product of a planned breeding program which had the objective of creating new chrysanthemum cultivars with decorative capitulum type, spreading branching habit, early flower response, and red-purple flowers, making it particularly suitable for production as a garden variety. Such traits in combination were not present or needed improvement in previously available commercial cultivars.

Empire Calypso was originated from a hybridization made by the inventor Janet S. Fuess in a controlled breeding progam in New Hartford, N.Y. in 1990. The female parent was Bordeaux, disclosed in U.S. Plant Pat. No. 6,987. The male parent of Empire Calypso was a pink decorative unnamed seedling identified as B88-2, a proprietary breeding line.

Empire Calypso was discovered and selected as one flowering plant within the progeny of the stated parentage by the inventor in August 1991 in a controlled environment in New Hartford, N.Y.

The first act of asexual reproduction of Empire Calypso was accomplished when vegetative cuttings were taken by the inventor from the initial selection in October 1991 in a controlled environment in New Hartford, N.Y. Horticultural examination of selected units initiated in September 1992 has demonstrated that the combination of characteristics as herein disclosed for Empire Calypso are firmly fixed and are retained through successive generations of asexual reproduction.

Empire Calypso has not been observed under all possible environmental conditions. The phenotype may vary significantly with variations in environment such as temperature, light intensity, and daylength, without, however, any variation in genotype. The following observations, measurements, and comparisons describe plants grown in New Hartford, N.Y. under natural outdoor conditions which approximate those generally used in commercial practice.

The following traits have been repeatedly observed and are determined to be basic characteristics of Empire Calypso, which in combination distinguish this Chrysanthemum as a new and distinct cultivar:

1. Red-purple ray florets.
2. Fully double flowers—no disc florets present.
3. Fully expanded ray florets are each approximately 2.0 cm long and 0.6 cm wide, with regular dentate tips.
4. Average of 223 ray florets per flower.
5. Capitulum diameter of 4.0–4.5 cm.
6. Seven week flower response in controlled light/shade programs.
7. Performs well in outdoor programs, flowering early (September 20) in natural season in New York.

8. Compact, mounded cushion habit.
9. Adaptability to greenhouse or garden cultures.

Of the many commercial cultivars known to the present inventor, the most similar in comparison to Empire Calypso is Sundoro, disclosed in U.S. Plant Pat. No. 7,225. In comparison to Sundoro, Empire Calypso has a smaller, more formal decorative flower form and a more freely branching growth habit. The seven week flower response in light/shade programs and reddish-purple flower color are similar to those same characteristics of Sundoro.

The accompanying color photographic drawing shows typical flower and foliage characteristics of Empire Calypso, with colors being as nearly true as possible with illustrations of this type.

In the following description, color references are made to the Royal Horticultural Society Color Chart. The color values were determined between 10:00 a.m. and 1:00 p.m. on Sep. 8, 1994 under 4,000 footcandles at New Hartford, N.Y.

Classification:

*Botanical.*—*Dendranthema grandiflora* cv. Empire Calypso.

*Commercial.*—Formal decorative garden mum.

INFLORESCENCE

Capitulum:

*Form.*—Decorative, with no disc florets.

*Type.*—Double.

*Diameter across face.*—4.0–4.5 cm, when fully open.

Corolla of ray florets:

*Color (general tonality from a distance of three meters).*—Red-purple.

*Color (upper surface).*—60B.

*Color (under surface).*—65B.

Reproductive organs:

*Androecium.*—None.

*Gynoecium.*—Present only on ray florets: style is 0.4 cm long and bifurcated.

PLANT

General appearance:

*Height.*—24–28 cm, when grown in an 8" pot.

Foliage:

*Color (upper surface).*—139A.

*Color (under surface).*—139B.

*Size and shape.*—4.5–6.0 cm long, 4.0–4.5 cm wide, 5-lobed.

It is claimed:

1. A new and distinct cultivar of Chrysanthemum plant named Empire Calypso, as illustrated and described.

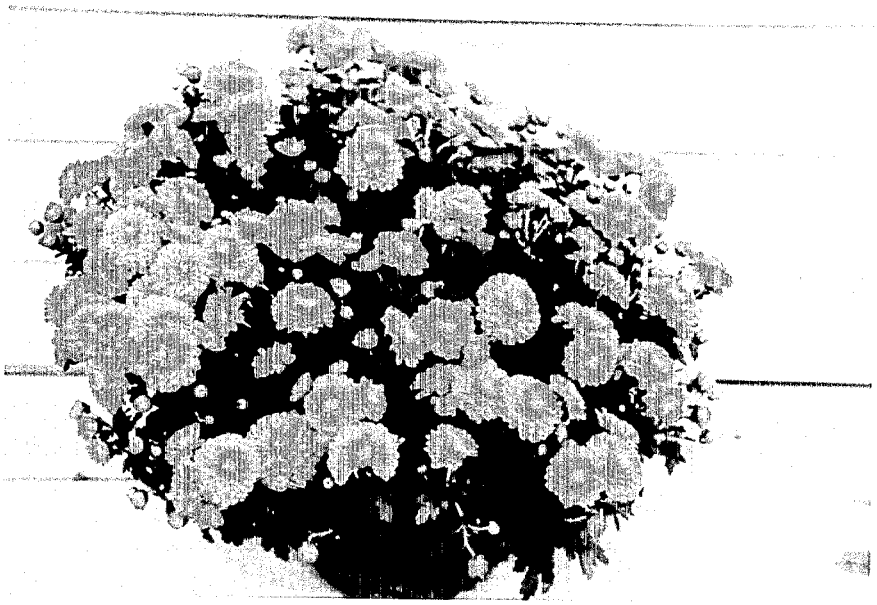

* * * * *